(12) United States Patent
Rousseau et al.

(10) Patent No.: US 9,999,354 B2
(45) Date of Patent: Jun. 19, 2018

(54) BIOLOGICAL TISSUE INSPECTION METHOD AND SYSTEM

(75) Inventors: Guy Rousseau, Ste-Julie (CA); Alain Blouin, Montreal (CA); Jean-Pierre Monchalin, Montreal (CA)

(73) Assignee: National Research Council of Canada, Ottawa (CA)

( * ) Notice: Subject to any disclaimer, the term of this patent is extended or adjusted under 35 U.S.C. 154(b) by 703 days.

(21) Appl. No.: 13/353,797

(22) Filed: Jan. 19, 2012

(65) Prior Publication Data

US 2012/0200845 A1    Aug. 9, 2012

Related U.S. Application Data

(60) Provisional application No. 61/434,943, filed on Jan. 21, 2011.

(51) Int. Cl.
  *A61B 5/00*    (2006.01)
  *G01N 21/17*   (2006.01)
  *G01N 29/24*   (2006.01)

(52) U.S. Cl.
  CPC .......... *A61B 5/0093* (2013.01); *A61B 5/0095* (2013.01); *A61B 5/0097* (2013.01); *A61B 5/0059* (2013.01); *G01N 21/171* (2013.01); *G01N 21/1702* (2013.01); *G01N 29/2418* (2013.01); *G01N 2291/02475* (2013.01)

(58) Field of Classification Search
  USPC ....................................................... 600/410
  See application file for complete search history.

(56) References Cited

U.S. PATENT DOCUMENTS 3,696,248 A * 10/1972 Cunningham et al. .... 250/203.2
4,121,890 A * 10/1978 Braun .......................... 356/4.02
(Continued)

OTHER PUBLICATIONS

Photoacoustic Imaging Endoscope by C. Sheaff et al. pub. 31st Annual International Conference of the IEEE EMBS Minneapolis, Minnesota, USA, Sep. 2-6, 2009.*

(Continued)

*Primary Examiner* — Katherine Fernandez
*Assistant Examiner* — Michael Kellogg
(74) *Attorney, Agent, or Firm* — Cermak Nakajima & McGowan LLP; Adam J. Cermak

(57) ABSTRACT

A method and system for inspecting biological tissue that has no applied coatings or treatments to improve reflectivity comprises an optical detection system with an exposed surface for inspection by an optical detection system; and a laser for exciting an ultrasonic wave within the tissue, which wave propagates within the tissue at least near the surface. The optical detection system includes: a laser to emit a pulsed detection laser beam onto the surface at a detection spot, the pulsed laser beam having a wavelength at which there is large scattering and little absorption by the tissue, and a pulse duration is chosen to correspond with ultrasonic propagation times associated with a range of depths of the scan, whereby the fluence of the detection laser is not applied unless ultrasonic information regarding a given depth is being obtained; and large étendue collection optics for collecting reflected and backscattered light from the detection spot; and a demodulator to extract information from the ultrasonic wave from the collected light.

20 Claims, 4 Drawing Sheets

(56) References Cited

U.S. PATENT DOCUMENTS

| | | | |
|---|---|---|---|
| 5,131,748 A | | 7/1992 | Monchalin et al. |
| 5,348,002 A | * | 9/1994 | Caro ............................ 600/310 |
| 5,680,212 A | | 10/1997 | Blouin et al. |
| 5,920,390 A | * | 7/1999 | Farahi et al. ................. 356/477 |
| 6,020,963 A | * | 2/2000 | DiMarzio ..................... 356/491 |
| 6,041,248 A | * | 3/2000 | Wang ............................ 600/407 |
| 6,128,092 A | * | 10/2000 | Levesque et al. ............. 356/451 |
| 6,213,958 B1 | * | 4/2001 | Winder .......................... 600/586 |
| 6,335,943 B1 | * | 1/2002 | Lorraine et al. ................ 372/28 |
| 6,390,978 B1 | * | 5/2002 | Irion et al. .................... 600/437 |
| 7,310,150 B2 | * | 12/2007 | Guillermo et al. ........... 356/479 |
| 2003/0172736 A1 | * | 9/2003 | Blouin et al. .................. 73/643 |
| 2006/0241572 A1 | * | 10/2006 | Zhou ................................ 606/7 |
| 2012/0010604 A1 | * | 1/2012 | Allen ............................. 606/14 |

OTHER PUBLICATIONS

Simultaneous multimodal imaging with integrated photoacoustic microscopy and optical coherence tomography by Shuliang Jiao et al. pub. Oct. 1, 2009 / vol. 34, No. 19 / Optics Letters.*

OSHA Technical Manual (OTM) Section III: Chapter 6, pub. online Effective Date: Jan. 20, 1999 by The United States Department of Labor.*

Three-dimensional photoacoustic imaging using fiber-based line detectors by Hubert Grun et al. pub. Journal of Biomedical Optics 15_2_, 021306 Mar./Apr. 2010.*

Berer et al., "Remote photoacoustic imaging for material inspection", 2nd international symposium on laser ultrasonics—Science, Technology and Applications, Jul. 5-8, 2010, Bordeaux France.

Blouin et al., "Detection of ultrasonic motion of a scattering surface by two-wave mixing in a photoreactive GaAs crystal", Appl. Phys. Lett. vol. 65, p. 932-934, 1994.

Duck F.A., "Medical and non-medical protection standards for ultrasound and infrasound", Prog. Biophys. Mol. Biol. vol. 93, p. 176-191, 2007.

Ing et al., "Broadband optical detection of ultrasound by two-wave mixing in a photorefractive crystal", Appl. Phys. Lett., vol. 59(25), p. 3233-3235, 1991.

Jacques et al., "Non-contact detection of laser-induced acoustic waves from buried absorbing objects using a dual-beam common-path interferometer", SPIE Proceedings, vol. 3224, p. 307-318, 1998.

Laser Institute of America, American National Standard for the Safe Use of Lasers ANSI Z136.1-2000 (ANSI Orlando, Florida, 2000), p. 62-78.

Monchalin, J.P., "Optical detection of ultrasound at a distance using a confocal Fabry-Perot interferometer", Appl. Phys. Lett., vol. 47(14), p. 14-16, 1985.

Monchalin, J.P., "Optical detection of ultrasound", IEEE Trans. Ultrason. Ferroelectr. Freq. Control., vol. 33(5), p. 485-499, 1986.

Oraevsky et al., "Two-dimensional opto-acoustic tomography transducer array and image reconstruction algorithm", Part of the SPIE Proceedings conference on Laser-Tissue Interaction X: Photochemical, Photothermal and Photomechanical, vol. 3601, p. 256-267, San Jose, California, Jan. 1999.

Payne et al., "Optoacoustic tomography using time resolved interferometric detection of surface displacement", Journal of Biomedical Optics, vol. 8(2), p. 273-280, 2003.

Scruby et al., "Fabry-Perot interferometers", Laser-Ultrasonics: Techniques and Applications, Taylor & Francis, p. 132-147, 1990.

Wang et al., "Photoacoustic tomography", Biomedical Optics: Principles and Imaging, John Wiley & Sons, chapter 12, p. 283-286, 2007.

Wang et al., "Noninvasive laser-induced photoacoustic tomography for structural and functional in vivo imaging of the brain", Nature Biotech., vol. 21(7), p. 803-806, 2003.

Zhang et al., "Photoacoustic ophthalmoscopy for in vivo retinal imaging: current status and prospects", Ophthalmic Surgery, Lasers & Imaging, vol. 42(4 suppl), p. S106-S115, 2011.

Programme for the scientific evaluation of the CD-Laboratory for Photoacoustic Imaging and Laser Ultrasonics, Oct. 19, 2010, Christian Doppler Forschungsgesellschaft, Wien, Austria.

Berer, T., et al., "Remote photoacoustic imaging on solid material using a two-wave mixing interferometer," Optics Letters 2010;35(24):4151-4153.

Application for the establishment and funding of a Christian Doppler Laboratory for Photoacoustic Imaging and Laser Ultrasonics (CD-Labor fuer Photoakustik und Laser-Ultraschall), Applicant: Peter Burgholzer, Linz, Austria, Jun. 2008.

* cited by examiner

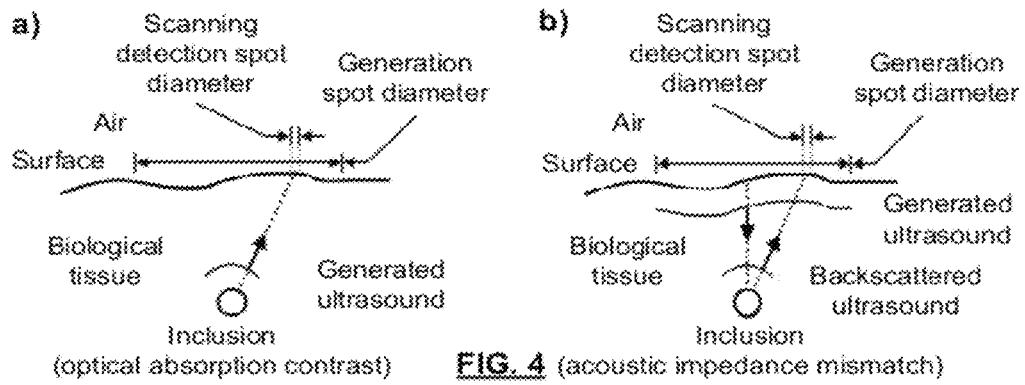
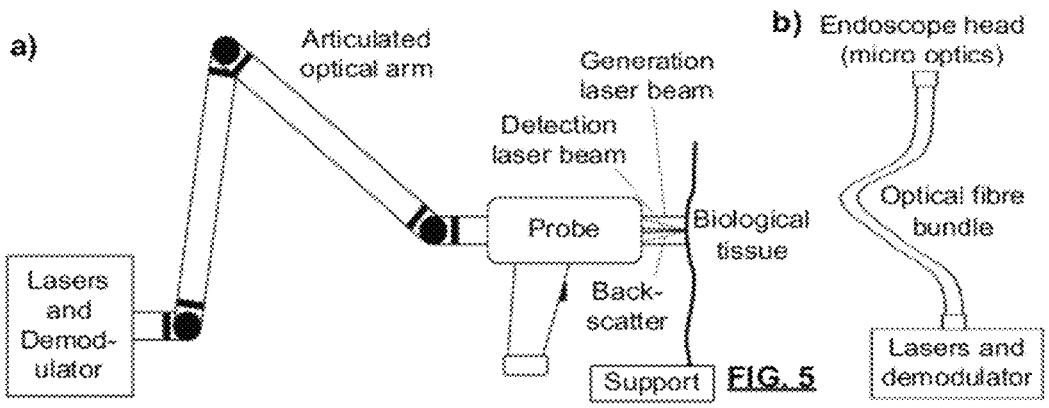
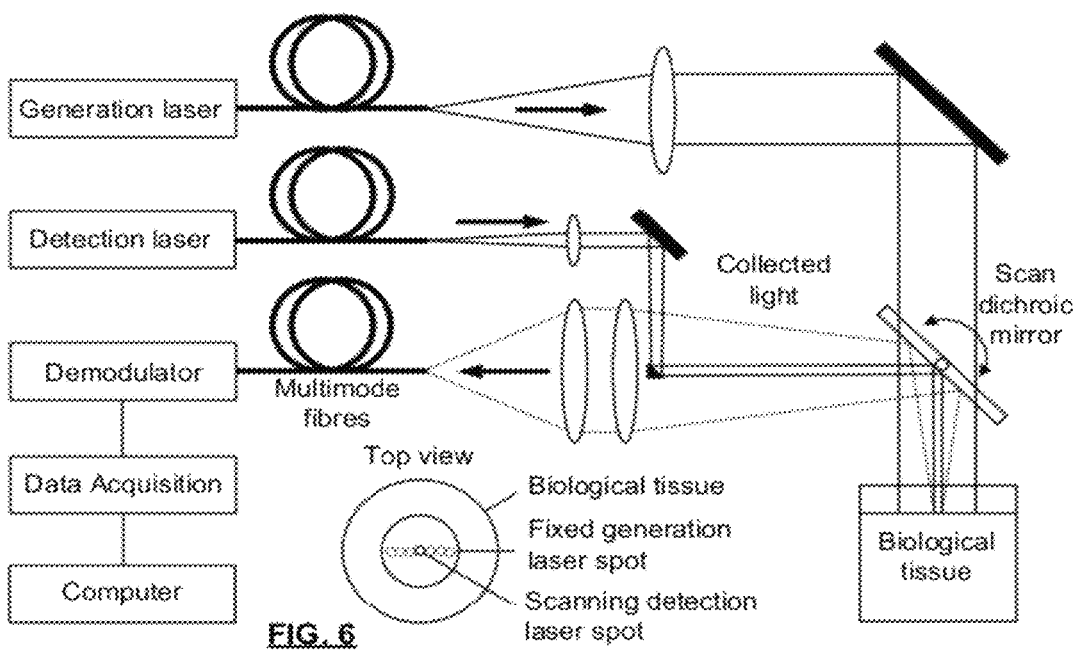

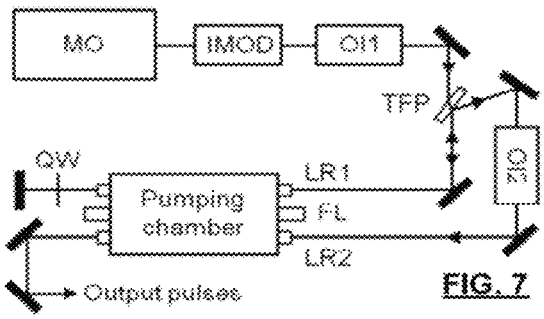
FIG. 7
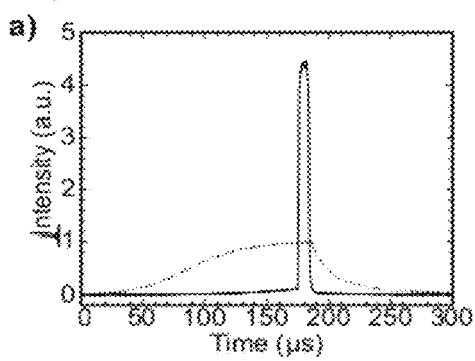
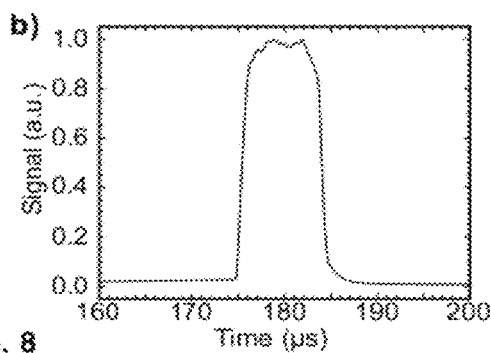
FIG. 8
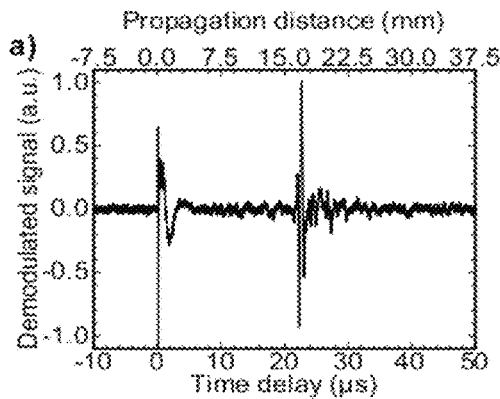
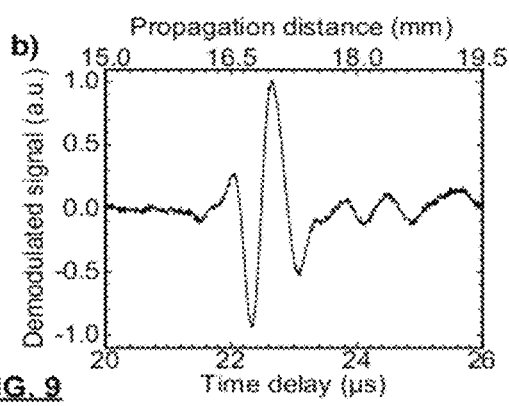
FIG. 9
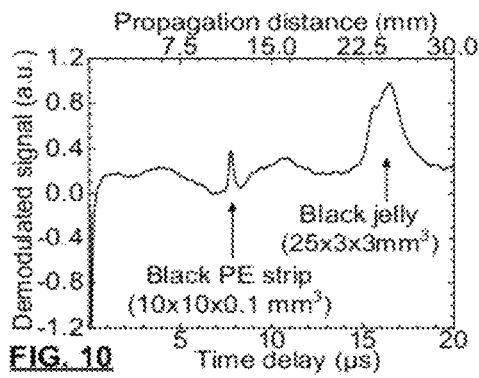
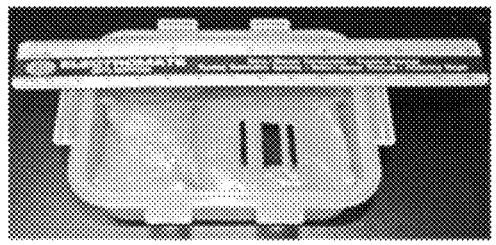
FIG. 10   FIG. 11

BIOLOGICAL TISSUE INSPECTION METHOD AND SYSTEM

FIELD OF THE INVENTION

The present invention relates to the field of biomedical imaging and, in particular, to a laser and ultrasound-based method and system for in vivo or ex vivo, non-contact imaging of biological tissue.

BACKGROUND OF THE INVENTION

Laser-ultrasonics is a well established technique first developed for the non-destructive testing of industrial materials like metals, plastics and polymer-matrix composite materials. A typical laser-ultrasonic system is composed of two lasers and a phase demodulator, as sketched in FIG. 1. In laser-ultrasonics, ultrasound is generated and detected at a distance. The ultrasound is usually generated on the surface of the material and the detection of ultrasound is performed on the same surface with a detection laser and a phase demodulator collecting the reflected and/or scattered light. Laser-ultrasonics can be applied to parts having complex shapes without any surface preparation and at high temperature. This technique has been shown to be applicable to real industrial conditions. In particular, the technology has been commercially developed for measuring on-line the wall thickness of steel tubes at 1000° C. moving at 4 m/s and for inspecting polymer-matrix composite materials used in aerospace.

The generation laser emits short optical pulses (from about 100 ns to 100 fs) to produce an ultrasonic wave at the surface of the sample by pure thermoelastic generation, or by thermoelastic generation coupled with some ablation of the surface material. The detection laser then illuminates the surface with a single frequency (or narrow linewidth), moderate power, very stable, long pulse laser. The laser pulse has a pulse duration between 50 and 200 microseconds. The peak power of the detection laser can exceed 1 kilowatt. The detection laser is usually based on a master oscillator power amplifier (MOPA) design which includes a very stable single frequency continuous wave (CW) laser oscillator followed by one or more optical amplification stages. Optical isolators are required between the master oscillator and the amplifying stages.

Light retroreflected or backscattered from the sample is then collected with a large étendue optical system and coupled to an optical phase demodulator. The wavefront insensitive demodulator is usually a confocal Fabry-Perot interferometer (CFPI) or a photorefractive interferometer (PRI). These phase demodulators are able to process beams with large étendue, which is an essential requirement in real applications where the beam reflected from the sample is strongly scattered by rough surfaces. The output signal from the demodulator is then digitally sampled by an acquisition card and processed by a personal computer.

The successful industrial applications reported above, as well as others, were made possible by detection schemes and technology that provide sufficient sensitivity. Adequate sensitivity is obtained by using a demodulator, such as a CFPI or a PRI, that has a large étendue and allows processing a collected beam with speckles. It requires receiving a significant amount of light from the surface, which is realized by having a collecting aperture as large as is practical (which means a large solid angle) and using a relatively high power detection laser. Having sufficient power detection laser contributes significantly to sensitivity since the more light is sent to the surface, the more is collected. In the case of industrial materials there is essentially no limit on the power or energy that can be sent for detection onto the surface, except in very special cases. Damage in industrial laser-ultrasonics is usually caused by ablation from the generation laser and not the detection laser.

On the other hand, biomedical optical imaging is presently a very active research and application area. Optical diagnostic techniques can be separated into several categories depending upon their sensitivity to optical properties of tissues, namely absorption, scattering or fluorescence and if they are based on the detection of essentially unscattered light (i.e. ballistic photons) or diffused light. Imaging technologies that rely on ballistic or quasi-ballistic (snakelike) photons include conventional microscopy as well as many of its variants such as confocal microscopy, phase contrast microscopy, and multiphoton spectroscopy. Those imaging methods rely on ballistic photons and are essentially limited by the light diffraction limit. Optical coherence tomography (OCT) relies also on the detection of backscattered ballistic or quasi-balistic photons. This technique still provides a high transverse resolution (typically of the order of 1 μm), a good depth resolution (typically 10 μm) but is limited in terms of the probing depth, typically 1 to 2 millimeters in biological tissue. Diffuse optical tomography (DOT) relies instead on the detection of diffuse photons but has a poor spatial resolution (1 cm is typical).

Optical imaging has been recognized to be a powerful biomedical imaging technique, that depends on scattering or absorption within the sample. For example, changes of reflection between tissue layers could indicate the presence of cancer or the accumulation of fat (e.g. underneath an artery wall). Blood vessels are readily detected by the optical absorption of blood and the optical absorption of oxyhemoglobin and deoxyhomoglobin indicate tissue perfusion and metabolism, as well as the presence of cancerous tumors (angiogenesis). Another application of interest is the probing of blood oxygenation in sensitive tissues, such as a retina's blood vessels. Inadequate oxygenation or oxygen consumption within the retina has been linked to many severe eye diseases causing loss of vision.

Biological and medical imaging of tissues also includes purely ultrasonic methods such as ultrasonography (US), which provides a lower resolution (of the order of 1 mm) but with a much higher penetration depth (typically 10 cm) owing to the low scattering of ultrasonic waves in biological tissue (compared to optical waves). Higher transverse resolution can be obtained using higher frequencies but at the cost of the penetration depth. Ultrasonic methods mainly provide information about the mechanical properties of tissue such as the stiffness and the density using reflections due to ultrasonic impedance mismatch between inclusions such as a tumors and the surrounding tissue. More recent innovations in ultrasonic imaging methods include Doppler US and more advanced image reconstruction methods.

Combining the optical contrast provided by optics with the deeper probing capacity of ultrasound has been recognized as desirable, and shown to be applicable in two different ways: using ultrasound-modulated optical tomography (UOT); and photo-acoustic tomography (PAT).

UOT involves ultrasonic waves produced by a conventional focused transducer usually in direct contact with the tissue using water as the coupling medium. The tissue is then illuminated with a single-frequency laser beam and light transmitted through the tissue is collected and analyzed with a large étendue optical system. The ultrasonic waves modulate the phase of light scattered by the tissue. Different implementations are based either on an extremely narrow optical band-pass filter (CFPI or cryogenic atomic filters using spectral hole burning in rare earth ion doped crystals), a photorefractive interferometer (PRI) in quadratic detection, or a CCD camera followed by suitable signal processing (parallel speckle imaging). The light interacting with the ultrasonic wave is tagged by a frequency shift equal to the ultrasonic frequency. Knowing the position of the ultrasound at any time from the known velocity of propagation and the position of the transducer, the tagged photons provide localized information about the optical properties of objects embedded in the biological sample. It has been shown that this method not only provides information on optical absorption but also on optical scattering.

PAT relies on ultrasonic waves generated optically within one or more localized regions (i.e. an optical absorber) inside a highly optically scattering biological tissue. A generation laser emitting short pulses (typical pulse duration of about 10 ns) is used to illuminate the tissue. Photons then propagate within the tissue following highly randomized optical paths, owing to the high concentration of natural optical diffusers (cells) in biological tissue. Energy from these pulses is absorbed by the optical absorbers, with much greater efficiency than the surrounding tissues. The absorbed heat results in thermal expansion of the optical absorber relative to the surrounding tissues. When the optical illumination is very short, the thermal expansion is sufficiently fast to produce ultrasonic waves emanating from the optical absorber. These ultrasonic waves then propagate in the tissue up to its surface, and a single scanning piezoelectric transducer or a matrix of piezoelectric transducers can be used to detect the ultrasonic waves with a given spatial resolution. Transmission of the ultrasonic waves to the scanning transducer or matrix of transducers requires some coupling medium, which is in practice a gel film applied onto the skin of the small animal or human patient, or a water bath in which the animal or human part is immersed. Mathematical techniques are then used to reconstruct the ultrasonic wave distribution at the time of the generation laser pulse illumination. This distribution corresponds to a three-dimensional mapping of the optical absorption of embedded optically absorbing inclusions.

These combinations of optical sensing and ultrasound require contact or fluid coupling of the ultrasound generation (in UOT) or detection (in PAT) device. There are obviously major drawbacks to applying PAT in some applications, such as small animal imaging where the water bath require immersing the animal with an air carrier (aerophore) as shown in FIG. 2. It is also cumbersome in the case of human breast imaging for the detection of cancer which is another application for which PAT has been developed. This coupling requirement also limits the application of PAT in the case of surgery or endoscopic examination. Furthermore non-contact techniques are desired when probing soft tissues such as an eye, especially in highly sensitive regions like the retina, or other layers in the eye. Non-contact detection by optical means in PAT, as done in industrial laser-ultrasonics, would obviously be desirable but is not feasible with prior art knowledge, essentially because of two opposing requirements: the requirement of using a high power detection laser to get sufficient detection sensitivity; and the requirement of using a low power detection laser to avoid damaging the tissue.

Some efforts to apply non-contact PAT to biological phantoms and tissues have been reported in the past, but the reported approaches have failed to be practical or could not produce adequate sensitivity in the case of a tissue that has not been provided a high reflectivity coating. For example "Non-contact detection of laser-induced acoustic waves from buried absorbing objects using a dual-beam common-path interferometer" by Jacques et al. (SPIE proceedings vol. 3224, pp. 307-318 (1998)) and "Optoacoustic tomography using time-resolved interferometric detection of surface displacement" by Payne et al. (Journal of Biomedical Optics, vol. 8, pp. 273-280 (2003)). In these reported works, low power He—Ne lasers were used, and detection was performed from the mirror-like surface of a liquid by using specular reflection, which means that the probing beam had to be normal to the surface. The phantoms actually used were liquid, either completely transparent or seeded with particles to get scattering properties similar to those of tissues for the generation laser beam. The demonstration of the detection of a blood vessel in the forearm of a human volunteer was also disclosed. The forearm was covered with a water layer a few mm thick. The vessel was only about 1 mm deep. In practice, it is desired to be able to detect inclusions (vessels, tumors) much deeper, certainly beyond the limit of OCT and on unprepared surfaces, such as the human skin, the surface of internal organs exposed during surgery or accessible from an endoscopic examination or the shaved skin of a mouse. These previous works do not teach or suggest that it was possible to apply non-contact PAT in such conditions.

So while non-contact PAT has been applied to industrial materials, in particular to the case of a translucent polymer bonded to metal, as reported in the Symposium on Laser Ultrasonics 2010 (see Remote Photoacoustic Imaging for Material Inspection by T. Berer, A. Hochreiner, B. Reitinger, H. Grün and P. Burgholzer, Journal of Physics, conference series 2010), this is because industrial materials have no effective limit on the detection laser power or energy. Existing non-contact PAT techniques do not teach how to apply non-contact PAT on biological tissue in vivo or ex vivo, and does not even suggest that this would be possible.

The conflicting requirements for high power signaling without damaging tissues have so far led to the conclusion that non-contact optical detection of ultrasonic waves on a living organism is not possible, and no such technique or system has been reported. More specifically, to avoid damage to the tissue, energy of the pulsed detection laser, spot size and number of pulses sent onto a given location have to be below the maximum permissible exposure (MPE). This limit for the 1.06 μm wavelength, which is the wavelength of a detection laser used in industrial laser-ultrasonics and for which high power can be obtained, is given (in $J/cm^2$) by the formula $1.1\ C_A\ t^{0.25}$ where $C_A=5$ and t is the pulse duration (in seconds) or the total duration of multiple pulses if signal averaging is used to increase sensitivity. This formula indicates for typical single pulse duration of 60 μs a value of about 0.48 $J/cm^2$ or 3.7 mJ over a spot of 1 mm in diameter (corresponding to a peak power of 62 W). Considering first only the reflection by the surface and assuming a tissue index of refraction of 1.35, about 2.2% of the incident light is then reflected. Assuming further a collecting aperture 1 cm in diameter located 10 cm away from the surface (collection half angle=0.05 rd) and a Lambertian scattering surface, the collected power is about 3.4 mW. If a confocal Fabry-Perot in transmission mode is used as a demodulator, the detection limit formula for shot noise limited detection is: $U_{lim,rms}=(\lambda/(4\pi S))\ (2\ h\nu\ B/(\eta\ I_{D0}))^{1/2}$, where $\lambda=1.06$ μm, hv is the photon energy (1.9×$10^{-19}$ J at 1.06 μm), S is sensitivity factor (about 1), B is the electronic bandwidth (taken to be 10 MHz), q is the quantum efficiency (about 0.9), and $I_{D0}$ is the power received by the detector (about ¼ the input power at the entrance of the confocal Fabry-Perot). This formula gives a detection limit equal to about 0.006 nm (rms). The detection limit in pressure is related to the particle displacement by: $P_{lim,rms} = \rho V_{ac} 2\pi f_u U_{lim,rms}/2$ where $\rho$ is the density (about 1000 kg/m$^3$), $V_{ac}$ the acoustic velocity (about 1480 m/s) and $f_u$ the ultrasonic frequency (taken to be 5 MHz). The factor 2 comes from the doubling of the displacement by reflection of the ultrasonic wave at the free surface. We find $P_{lim,rms} = 140$ Pa = 1.4 mbar. This value is of the order of what could be produced in PAT (see 12.3 in *Biomedical Optics*, a textbook by Lihong Wang and Hsin-I Wu, John Wiley & Sons 2007). Therefore the sensitivity calculated based only on the reflection of the surface of the tissue, assuming maximum permissible exposure for 1 mm spot size and other design parameters but neglecting all transmission losses through the various optical elements, is barely sufficient. To be able to receive a signal above the noise, several of the parameters used above will have to be modified, for example if one accepts to double the spot size, incident power could be multiplied by 4 and sensitivity doubles but resolution will be diminished. One notes also that sensitivity is far below what is obtained with piezoelectric detection, which is about 0.5 Pa (Oraevsky et al, Proceedings SPIE vol 3601, 1999).

The calculation above considers only the reflection or scattering by the surface of the tissue but it is known that much more light is backscattered by the internal inhomogeneities of the tissue. However only a fraction of this backscattered light is contributing to the phase modulation signal since a scattered photon has to go through the illuminated surface spot where it originates and to exit within a limited solid angle to be collected. Since there is a small probability for these events to occur, the contribution of the internally scattered light will be small. In addition, as explained below, there are other reasons that make the contribution of the internally scattered light small, even by taking into account the increase of light energy density close to the surface of the tissue (of the order of the light penetration depth, i.e. in practice, of the order of 5-10 mm, see for example section 3.6.3 in *Biomedical Optics*, a textbook by Lihong Wang and Hsin-I Wu, John Wiley & Sons 2007, cited above).

Subsurface phase modulation comes from two effects associated with the ultrasonic wave: the displacement of the scattering centers and the modulation of the index of refraction. The displacement contribution is similar to the surface contribution. If the spatial extent of the ultrasonic wave is longer than the through-depth extent of the effectively collected photon cloud, all the scattering centers have the same motion as the surface, and the contributions of all internally scattered photons is added to that of the surface, thus producing increased sensitivity. If the ultrasonic pulse is generated at one or a few absorbers, e.g. in the case of PAT-like excitation, in general this condition is not met. It would require an exceptionally large absorber (e.g. very large tumor) relative to the detection spot size or some very particular absorber, surface, and internal acoustic structure to generate a relatively uniform ultrasonic wave across the extent of the effectively collected photon cloud. In the more general case of an ultrasonic wave with a spatial extent smaller than the effectively collected photon cloud, phase shift is due to a moving slice of thickness about equal to the size of the inclusion (e.g. tumor). Mathematically the displacement response of the inclusion is convoluted with the effectively collected photon cloud which entails that high frequencies are cut off. The duration of the received signal is then, in this case, equal to the through-depth extent of the effectively collected photons cloud divided by the acoustic velocity. Thus in the cases of interest, when PAT-like excitation is used, the contributions of the scattering center motion are not indicative of the size of the inclusion, which is critical diagnostic information.

Regarding now the index of modulation mechanism, it should be first noted that this effect is opposite to the one produced by the surface motion, since increasing the pressure causes an increase of the refractive index and thus lengthens the path length and gives an additional delay. Due to the bipolar nature of the pressure caused by ultrasonic waves, there is a cancellation effect, unless the ultrasonic wave extent is larger than the through-depth of the effectively collected photon cloud. In this case, since the surface is free, there is reflection of the pressure wave with an opposite polarity, giving an additional cancellation effect.

As a conclusion regarding the contribution of the internally scattered photons, only a small fraction of them is expected to contribute to the signal and their small contribution will be essentially at low frequencies (below 1 MHz) and may not relate to the size of the inclusion. Signals that provide information on the size of an inclusion will be essentially given by light only scattered by the surface of the tissue.

It would therefore appear inevitable that the sensitivity of optical detection of ultrasonic waves in tissues under non-damaging conditions is generally insufficient, and this confirms the belief that non-contact detection and therefore non-contact imaging of biological tissues using PAT-like excitation is expected to be infeasible, regardless of how desirable it would be.

SUMMARY OF THE INVENTION

Applicant has discovered that there are operating conditions for optical detection of ultrasonic waves in biological tissues (either ex vivo or in vivo) that provide both safety and adequate sensitivity. There are several applications envisaged for the optical detection of ultrasonic waves in tissues: non-contact PAT (NCPAT), where ultrasonic excitation comes from one or a few localized optical absorbers in the tissue and a mathematical process is used to determine their location and extent, and non-contact US (NCUS) where excitation comes essentially from the surface of the tissue and a mathematical process is used to determine the location and extent of acoustic discontinuities within the tissue. Advantageously, these methods can be applied in situations where contact is dangerous or impossible, such as in brain surgery, eye surgery, retinal diagnostics (with detection off the retina, or another layer within the eye), and in endoscopic applications. Applications are envisioned where surface preparation to couple ultrasound or optical beams is not practical: small animal imaging, surgery, endoscopic examination, burn diagnostic, or PAT combined with mammography to better localize vascularization around tumors. While the biological tissues chiefly considered for this application are soft tissues, such as brain, liver, lungs, skin, muscles, ligaments connective tissues, etc., any tissues that include absorbers, including blood, hemoglobin, deoxyhemoglobin, etc. and propagate ultrasound with sufficient efficiency, can be subject to the NCUS and NCPAT imaging or detection techniques.

Specific operating conditions involve permissible use of high detection laser power, with a large étendue demodulator, wherein the wavelength is chosen to provide little absorption, and the pulse duration is minimized, to effectively provide concentrated power.

The less absorbing the laser wavelength, the higher a dose is permitted, effectively ensuring a higher MPE. For example, choosing detection at 1.06 μm (fundamental of Nd-YAG laser) instead of 532 nm (frequency-doubled Nd-YAG) for which absorption is much stronger, allows a 5 fold increase in MPE. Using a wavelength longer than 1.5 μm and below 1.8 μm gives an even higher MPE: 1 J/cm$^2$ compared to 0.5 J/cm$^2$ calculated above.

The pulse duration is made as short possible to increase the peak power for optimum sensitivity. In the wavelength range 0.4 to 1.4 μm, and particularly at 1.06 μm, the MPE scales as $t^{0.25}$, therefore the peak power scales as $t^{-0.75}$, and the detection limit as $t^{0.375}$. For the wavelength range of 1.5-1.8 μm, peak power and detection limit scale as $1/t$ and $t^{0.5}$, respectively. However, pulse duration is constrained by the desired probing depth. Depending on the generation scheme used, the desired depth/acoustic velocity (NCPAT) or twice desired depth/acoustic velocity (NCUS) may be prescribed for efficient detection. A pulse duration of 10 μs gives a limit probing depth of about 15 mm for NCPAT and 7.5 mm for NCUS, which should be more than sufficient for many detection applications. By limiting the detection laser pulse duration, all the light from the detection laser is used and there is no unused light that contributes to exposure risk.

In the cases in which a single A-scan signal is sufficient for providing image, or detection information, and high lateral resolution is not required, ultrasonic signals are simply recorded and no further processing is performed. In other cases a sufficiently high resolution image (resolution better than 1 mm) is required. In such cases, a small detection spot is scanned over the surface of the tissue and synthetic imaging, using for example the synthetic aperture focusing technique (SAFT) algorithm, is used for image reconstruction and provides high resolution B-scan or C-scan images.

For NCPAT, the source of ultrasound is preferably at the inclusion, so reconstruction consists in summing A-scans delayed by the propagation time from the inclusion to the detection spot where the A-scan is collected. For NCUS, the source of ultrasound is at the surface (or close to it), so reconstruction involves summing A-scans delayed by the propagation time from the inclusion to the detection spot plus the propagation time from the surface to the inclusion. Since the surface of the tissue is not perfectly flat, improved imaging is obtained by measuring its topography with an optical ranging device and by taking into account the surface profile during image reconstruction. A technique that can be advantageously used for this purpose is OCT since the OCT beam can be easily sent collinearly with the detection laser beam using dichroic optics. The information provided by OCT on the tissue characteristics down to about 2 mm below the surface can also be advantageously displayed at the same time as the NCUS/NCPAT information.

Accordingly a method for inspecting biological tissue is provided, the method comprises providing biological tissue to be scanned to detect ultrasonic waves passing therethrough, and immobilizing an optical detection system with respect to the biological tissue with an exposed surface for inspection by the optical detection system, wherein the surface is not treated or coated to improve its reflectivity: exciting an ultrasonic wave within the tissue, that propagates within the tissue at least near the surface; and using the optical detection system to: emit a pulsed detection laser beam onto the surface at a detection spot, the pulsed laser beam having a wavelength at which there is little absorption by the tissue, and a pulse duration is chosen to correspond with ultrasonic propagation times associated with a range of depths of the scan, whereby the fluence of the detection laser is not applied unless ultrasonic information regarding a given depth is being obtained; collect reflected and back-scattered light from the detection spot with large étendue optics; and demodulate light collected from the detection spot, to extract information from the ultrasonic wave detected at the detection spot. The biological tissue may be in vivo or ex vivo. The pulse duration may be associated by a time delay from the generation pulse to correspond with a subsurface depth range.

The ultrasonic wave is preferably excited without contact. For example, the ultrasonic wave may be excited noninvasively by absorption of light from a pulsed generation laser beam extending over a large area of the surface in comparison with a size of the detection spot. Preferably, the wavelength of the generation laser may give distributed absorption near the surface, providing thermoelastic ultrasonic generation without ablation. Alternatively, or additionally the wavelength of the generation laser is such that light penetrates into the tissue and generates ultrasonic waves at optical absorbers within the tissue. If so, spectroscopic information about the optical absorber is obtained by using several generation lasers with different wavelengths or a generation laser with a tunable wavelength.

Exciting and using may be repeated, and information regarding the ultrasonic wave may be recorded at different locations on the surface, to generate an image of the ultrasound within the tissue. Imaging may be obtained by scanning the detection laser spot over the surface of the tissue and applying SAFT to obtain B-scan or C-scan images. SAFT reconstruction may be improved by taking into account surface topography which is measured with a profilometer, range finder, or by Optical Coherence Tomography. The information provided by Optical Coherence Tomography as well as information regarding the detected ultrasonic waves are simultaneously displayed and fused in a multimodal image. Alignment of the spot data to form an image may be provided by an optical scanner, or by a position tracking system, such as a vision-based position tracking system.

The optical detection system may be mounted within an endoscope.

For example, the detection pulse duration may be less than 20 μs, the detection pulse laser wavelength may be 1-2 μm, and the energy density may be optimized in accordance with the safety limits (MPE) for biological tissues.

Also accordingly, a system for inspecting biological tissue is provided. The system includes: a biological tissue immobilization apparatus for immobilizing the biological tissue to be scanned to with respect to an optical detection system, such that a surface is exposed for inspection by the optical detection system to detect ultrasonic waves passing therethrough, wherein the surface is not treated or coated to improve reflectivity of the laser beam; a contact-free ultrasonic wave excitation apparatus for generating ultrasonic waves within the tissue, that propagates within the tissue at least near the surface; and the optical detection system comprising: a pulsed detection laser for emitting a beam onto the surface at a detection spot, the pulsed laser beam having a wavelength at which there is little absorption by the tissue, and a pulse duration is chosen to correspond with ultrasonic propagation times associated with a range of depths of the scan, whereby the fluence of the detection laser is not applied unless ultrasonic information regarding a given depth is being obtained; large étendue optics to collect reflected and backscattered light from the detection spot; and a demodulator for deriving information from the ultrasonic wave detected at the detection spot. The short pulse detection laser may be obtained by limiting the duration of an electrical pulse feeding a pumping flashlamp or a pumping laser diode in a single or multistage optical amplifier coupled to a single frequency continuous wave master oscillator, or by adding an electro-optic modulator, an acousto-optic modulator or any optical switch between the single frequency continuous wave master oscillator and an optical amplifier. The system may further comprise a pulse shaping component for the detection laser, to compensate for tissue ultrasonic absorption as the ultrasonic wave propagates from the source to the surface, and for variation in ultrasonic wave excitation.

The demodulator may comprise a confocal Fabry-Perot interferometer (CFPI), a PRI, or an atomic filter such as a cryogenically cooled rare-earth ions-doped crystal.

The pulse duration may be associated by a time delay from the generation pulse to correspond with a subsurface depth range.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which:

FIGS. 4a),b) are schematic illustrations of ultrasonic wave pathways considered when using SAFT processing respectively in NCPAT and NCUS imaging modes;

FIGS. 5a),b) are schematic illustrations of two probe embodiments a) for a handheld operation and b) for medical procedures using an endoscope;

FIG. 6 is a schematic view of an embodiment for probing biological tissues in NCPAT and NCUS imaging modes;

FIG. 7 is a schematic view of the detection laser using a CW master oscillator followed by a multipass optical amplifier;

FIGS. 8a),b) are graphs respectively showing a comparison of the output pulse temporal profiles of a Nd:YAG detection laser with and without the use of an electro-optic intensity modulator, and an enlarged view of the shortened and shaped pulse;

FIGS. 9a),b) are graphs respectively showing a typical A-scan from a measurement in presence of an acoustic inhomogeneity (steel plate) embedded in a chicken breast and an enlarged view of the main ultrasonic echo;

FIG. 10 is a graph of a typical A-scan from a measurement obtained in presence of optical absorbers embedded in a chicken breast;

FIG. 11 is a photograph of absorbing objects embedded in a chicken breast, used for the demonstration of the NCPAT imaging mode;

DESCRIPTION OF PREFERRED EMBODIMENTS

A technique is described for non-contact detection of ultrasonic waves propagating in biological tissues.

Figure 1:
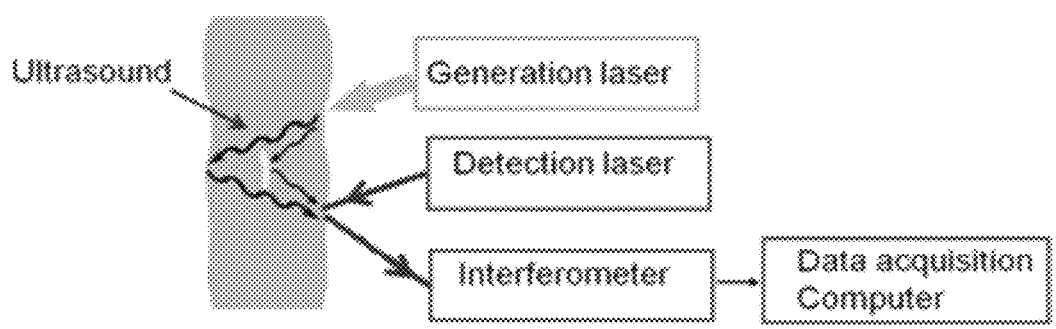
FIG. 1 is a schematic view of a prior-art laser-ultrasonic system.
Figure 2:
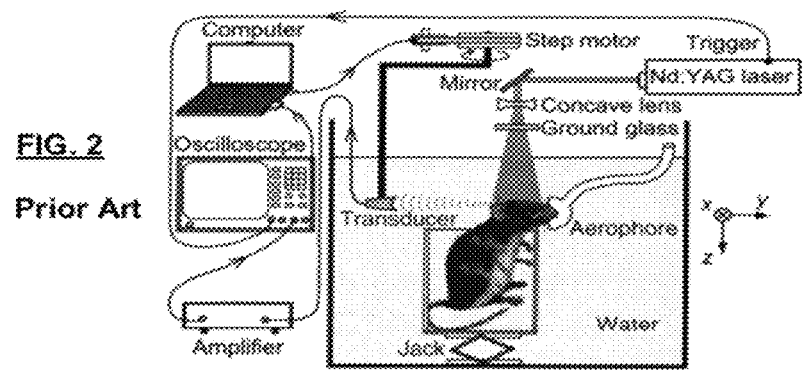
FIG. 2 is a schematic view of a prior-art PAT setup applied to brain imaging of a small animal.
Figure 3:
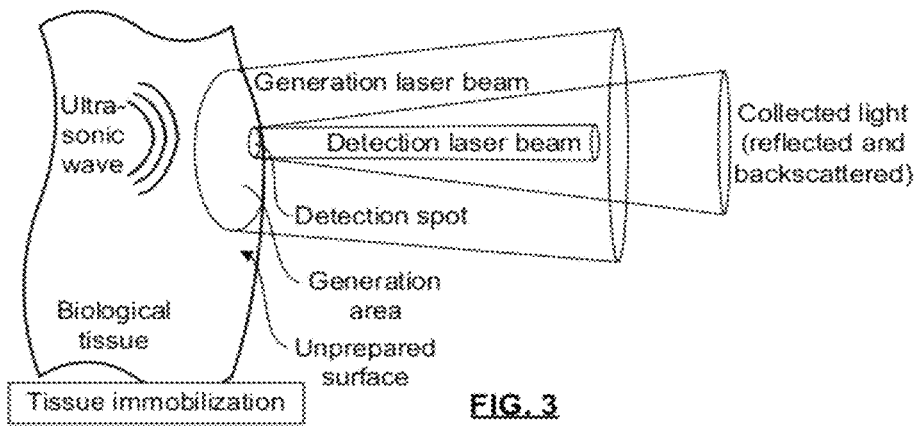
FIG. 3 is a schematic view of the geometry of pulsed laser light beams and collected beam involved in the non-contact implementation of PAT and US.

A schematic diagram of a preferred embodiment is shown in FIG. 3. A biological tissue (BT) of human or animal origin, either in vivo or ex vivo, has an unprepared surface. The BT is immobilized with respect to the examination equipment in any of the various ways known in the art, to stabilize the BT. Immobilization is required only for the duration of the scan, and therefore if the scan is quick, and the tissue is structurally supported, then immobilization may be effectively provided by supporting the equipment with a table in the same room as the tissue. The tissue immobilization may be provided by placing the tissue in a dish or plate, and preventing it from moving during the scan. The scan may be a very short A scan, in which case the scan may be expected to work even with some motion, and a hand-held probe can be used. Longer B scans may require some equipment for mapping the distances to present the scan information in a registered manner, but still may be provided by hand-held probe. C scans may require more registration but may not require any clamping or contact with the tissue. For surgical interventions, bodies are generally immobilized to a much higher degree than required for imaging or inspection according to the present invention. For endoscopic applications, sufficient immobilization is generally provided with known means.

A short pulse (typically 5-20 ns, but for some tissues, laser wavelengths and GLB power, it may range from 1-50 ns) generation laser beam (GLB) illuminates the surface on a generation area, which is typically of a largest size available for the tissue to be imaged, so a diameter of about 2 cm for small mammals, or larger areas for larger mammals. The wavelength of the GLB is chosen to be within the optical window of biological tissues that is between about 500 nm and 1000 nm in order to increase the probing depth of the photons. Due to the BT composition (cells and other optical scatterers), the GLB is strongly scattered. Most photons are backscattered just below the surface and are lost in air after only a few scattering events. The remaining photons penetrate more deeply into the BT, following highly randomized optical paths. Photons of the GLB will thus produce ultrasonic waves in two different ways. Firstly, any residual absorption of GLB photons backscattered in the immediate vicinity below the surface, where the power density is much higher, will generate an ultrasonic wave by thermoelastic generation. This produces an ultrasonic wave (UW) with a wavefront similar to the surface topography having a lateral extent given by the GLB diameter. After propagation, this UW will be scattered by any acoustic inhomogeneity within the BT, thus leading to backscattered ultrasonic waves. Secondly, GLB photons diffusely propagating more deeply inside the BT will also produce ultrasonic waves in presence of any optical absorber. Those ultrasonic waves then propagate throughout the BT in all directions until they reach the unprepared surface. The surface is monitored with a pulsed detection laser beam (DLB) which is generally focused on a smaller area than the generation area (typically $1/10^{th}$ to $1/100^{th}$ or more) in order to provide a spatially resolved temporal measurement of the surface displacement at discrete locations. These measurements are then used to generate a 2D or 3D image characterizing the tissue by using mathematical procedures known in the art. The DLB has a wavelength larger than 1 µm due to the higher tolerance of BT to laser exposure at wavelength above 1 µm, and particularly a wavelength from 1-1.8 µm, and more preferably 1.5-1.8 µm (ref. 10). The wavelength of 1.06 µm is often preferred due to the availability of suitable laser sources already developed for previous-art industrial and metrology applications. The biological nature of the tissue restricts the amount of laser energy which can be used for both the GLB and the DLB, however because the GLB is not constrained by the resolution of the image, the DLB fluence is critical. The pulse duration of the DLB is thus chosen to reduce the tissue exposure to laser light. Depending on an intended scan depth, or range of depths to be scanned, a corresponding pulse duration is required. The pulse duration corresponding to a range of depths may be triggered at a time delay correspondence to the ultrasonic propagation time (e.g. ~1.5 mm/µs), from the surface to the depths, in a manner well known in the art. Reducing the pulse duration allows increasing the peak power incident on the medium, thus increasing the sensitivity of the measurement. Typically, the DLB pulse duration will be less than 20 µs, corresponding to a propagation distances between 15 to 30 mm in typical BT. For applications in which the depth range of interest is much shorter, e.g. probing vascularisation within eye retina with detection directly off the retina surface, off adjacent layers within the eye or even from the surface of the blood vessel, the DLB pulse duration could be as short as 1 µs or shorter. DLB light which is reflected/backscattered by the BT is collected using a large étendue optical system and processed by embodiments known in the art.

The large étendue collecting optical system may be coupled to a multimode optical fiber of comparable étendue. Typically, an optical fiber with a core diameter of 1 mm or below and a numerical aperture (NA) below 0.4 will be sufficient. This corresponds to a maximum étendue $U_{max}=(\pi \varphi NA/2)^2=0.4$ mm$^2$sr, where $\varphi$ is a core diameter of the optical fiber. Such a value is comparable to the étendue of known optical demodulators such as a CFPI (50 to 100 cm long cavity) or a PRI. Phase demodulation with spectral hole burning in cryogenically cooled rare-earth ions doped crystal would also be suitable but more complex to implement, especially because of the difficulty of matching the atomic filter wavelength to that of the DLB.

The mathematical processing related to backscattered ultrasonic waves or PAT-like emitted waves are both known in the art. The two imaging modalities may be both employed for analysis of a same signal. Both imaging modalities are schematically illustrated in FIGS. 4a),b). Firstly, imaging in NCPAT mode, like in conventional PAT, will provide information on the location and the extent of optical absorbers (inclusions) embedded in the biological tissue, by generating an opto-acoustic wave. In this case, schematically shown in FIG. 4a), the ultrasonic wave is coming from the inclusion to the surface, and corresponding SAFT reconstruction relies on the one-way time of flight between the optical absorber and the surface (dotted line in FIG. 4a)). Secondly, imaging in NCUS mode will provide information on the location and extent of acoustic discontinuities (inclusions—though may be entirely different from the absorbers of FIG. 4a)) within the BT. In this case, schematically shown in FIG. 4b), the time of flight in the SAFT algorithm is the sum of the time of flight of the ultrasonic wave from the surface to the discontinuity and that of the backscattered ultrasonic wave from the discontinuity to the surface (dotted line in FIG. 4b)). For both imaging modalities, the topography of the surface must be taken into account for a better reconstruction. In most real applications, embedded objects or inhomogeneities will present both acoustic impedance mismatch and optical absorption contrast with the surrounding medium. The use of both image reconstruction algorithms will thus provide two types of information on each embedded object. The choice of the GLB wavelength as well as the intrinsic properties of the BT will also influence the relative strength of the backscattered ultrasonic wave and the opto-acoustic ultrasonic wave.

FIG. 5 schematically illustrates two envisioned systems which could be easily derived from the preferred embodiment for applications for in situ diagnostics on unprepared surfaces of biological tissues, during examinations or surgical procedures as well as for small animal diagnostics performed in research laboratories. FIG. 5a) shows a drawing of a handheld probe linked to the main laser system by an articulated optical arm including folding mirror and relay lenses, or an optical fibre to provide a continuous waveguide at any state of extension. The user would scan the surface, either manually (with a tracking system based on position encoders or by image tracking of the detection spot with a CCD camera) or with a scanning device inside the handheld probe. From the tracked position an image (B-scan or C-scan) can then be constructed. The second implementation shown in FIG. 5b) uses a fiber optic bundle ended by micro-optical components in order to perform NCUS and NCPAT diagnostics on parts of the body accessible through the mouth, the respiratory airway, the gastro-intestinal track, or other orifices, or through small incisions in the skin for less invasive surgical procedures.

The application to retinal diagnostics may involve directing the GLB and DLB essentially unscattered through the cornea to the retina. A signal related to the absorption of the GLB by blood in a vessel is obtained by detecting the reflection or scattered light from the DLB off the interface retina-vitreous humour or the surface of the vessel itself or any interface between the various layers at the back of the retina (retinal pigmented epithelium, choroid and sclera). Detecting directly off the surface, the surface motion of the vessel at ultrasonic frequencies, requires the shortest duration of the DLB, since this motion may occur very quickly. The duration of the surface motion of the vessel varies with the size of the vessel and the penetration of the GLB in blood. Its duration is calculated to be below 50 ns when the GLB is at 532 nm and therefore, a suitable duration of the DLB of 1 µs and even shorter is preferred. This short duration allows for the use of higher peak power, which translates into higher sensitivity, as mentioned above. Calculations we have performed, which are similar to one indicated above, have shown that probing blood oxygenation with non-contact detection off internal layers of the eye is feasible and could be performed safely. These calculations, the experimental results obtained so far, and ocular safety limits (see [10]) support the conclusion that NCPAT and NCUS can be used for retinal diagnostics. Such an approach advantageously replaces detection with an ultrasonic transducer contacting externally the eye, as reported in [15].

Example

FIG. 6 is a schematic illustration of a system used to verify the present invention. The generation laser was a frequency doubled actively Q-switched laser emitting 5 ns pulses at 532 nm. This wavelength efficiently excites blood, making it an effective ultrasonic transducer by thermoelastic generation. The repetition rate was equal to 10 Hz and the pulse energy impinging on the surface was about 100 mJ. The GLB was oriented toward a BT onto a large spot size (about 25 mm in diameter giving an area of 5 cm$^2$) which satisfies the maximum permissible exposure (MPE) at generation wavelength (20 mJ/cm$^2$ at 532 nm). With a 10 Hz repetition rate, the average power density of the GLB was equal to 200 mW/cm$^2$, which is also in accordance with the safety limit in the case of repetitive exposure at 532 nm. The detection laser beam was transmitted by a second optical fiber and focused onto the surface of the tissue after reflection by a computer controlled scanning mirror. The DLB had a wavelength $\lambda$ of 1.06 µm. The pulse duration was set according to the maximum ultrasound propagation time for the desired probing depth and the peak power and the laser power was set to approach the safety limit as described above. Scattered light was collected by a confocal Fabry-Perot interferometer (CFPI) used in transmission mode. The transmission mode was chosen for its higher sensitivity at low frequencies (below 10 MHz). A 1 meter long CFPI was used with mirror reflectivities R=94.5%, giving a finesse $F=\pi R/(1-R^2)=28$ and an optical étendue estimated as $U=\pi^2 L\lambda/F=0.375$ mm$^2$sr, where L, the length of the CFPI cavity, is 1 m. The experiments used two collecting optical fibres. The first had a core diameter $\varphi=1$ mm and a numerical aperture NA=0.39, giving an étendue $U=(\pi\varphi NA/2)^2=0.375$ mm$^2$sr comparable to that of the CFPI. The second optical fibre, used in other experiments, had a NA=0.36 and $\varphi=0.4$ mm, thus giving U=0.051 mm$^2$sr. As shown in FIG. 6, the coupling of the DLB in front of the collection optics ensures good separation between illumination and collection, and avoids stray light from illumination being coupled into the detection channel. The inset in FIG. 6 shows schematically a top view of the sample, of the large size generation area and of the scanned small detection spots. Although the embodiment used a mirror scanning the detection spot, it also possible to have a configuration in which a larger detection spot is not scanned.

As shown in FIG. 7, the detection laser used in our implementation was composed of a master oscillator (MO) which was a commercial continuous wave single-frequency Nd:YAG laser emitting about 200 mW at 1064 nm followed by a multipass flashlamp pumped Nd:YAG amplifier. An intensity modulator (IMOD: electro-optic modulator in our implementation) was located between the MO and the amplifier. The electrical signal feeding the IMOD was tailored to produce a top hat temporal profile of appropriate duration. The amplifier was a three-pass configuration using two Nd:YAG laser rods (LR1 and LR2 located in a pumping chamber including a flashlamp (FL) seeded by a variable pulse length power source (not shown). Two optical isolators were used: the first one (OI1) was located between the IMOD and the amplifier to protect the MO from any unwanted optical feedback from the amplifier, the second one (OI2) was located before the third stage of amplification to eliminate self oscillation of the amplifier and the accompanying relaxation oscillations. The quarter-wave plate (QW) and the thin-film polarizer were used in combination to use the LR1 for the first two amplifying stages. Short pulse duration (shown in FIG. 8) is obtained by using the electro-optic IMOD between the master oscillator and the optical amplifier. Alternatively the switch could be introduced at the output of the amplifier, although having it located before amplification is generally more efficient for extracting the energy stored in the amplifier while tailoring the temporal shape of the output pulse. Alternatively also, pulse shortening can be obtained by limiting the duration of the electrical pulse feeding the pumping flashlamp(s) or the pumping laser diode(s) in the single or multistage optical amplifier. In such a case, however, the pulse shape is primarily determined by the pumping flash temporal profile and the amplifying medium dynamics (laser transition lifetime). Tailoring the temporal profile of the detection laser pulse can also be used to compensate for tissue ultrasonic absorption and limited GLB penetration by having power increasing with time. This is equivalent to time-gain compensation (TGC) used in conventional ultrasound. The detection laser pulse energy is thus used optimally to obtain the best sensitivity while minimizing the exposure to laser light.

With each laser shot, an A-scan signal is obtained. The scanning mirror (one-axis or two-axis) allows scanning over the surface and then from the A-scan signals, B-scans and C-scans can be plotted as in conventional US. Reconstruction techniques such as SAFT and back projection algorithms are used to get higher resolution, two-dimensional (2D) or three dimensional (3D) mapping of embedded inclusions or anomalies within the tissue.

Results

The embodiment described above without the scanning mirror was used to demonstrate the NCUS and NCPAT diagnostic modes on a phantom having similar optical properties as human or mouse tissue. This phantom was made of pieces of raw chicken breast with inclusions such as a steel plate, black polyethylene (PE) strip or black jelly embedded from 10 to 20 mm deep below the surface. FIG. 9 shows the results obtained for the NCUS mode in which the phantom surface was slightly tinted with red dye to simulate the presence of blood at its surface. An echo coming from the steel plate is easily visible at time delay of approximately 22 µs, which corresponds to a propagation distance of about 17 mm. The size of the detection spot was about 3 mm in diameter.

The same system was also used in NCPAT mode. The inclusions in the phantom were a piece of black jelly of 25×3×3 mm$^3$ and a thin sheet of black polyethylene strip located respectively at about 23 mm and 12 mm below the surface. In this case, no red dye was used on the surface of the tissue, thus allowing the generation laser pulse to illuminate the whole volume of the sample. The demodulated signal is shown in FIG. 10. A first peak is seen at a time delay of about 8 µs, corresponding to the depth of the black strip. The second peak, which is wider, is located at a time delay of about 17 µs, also corresponding to the known depth of the black jelly. In this case, the duration of the peak is much longer since every point of the long jelly sample acts as an ultrasonic wave source. Consequently, points at both extremities contribute to the signal at long delays whereas the point at the center corresponds to the shortest propagation delay.

Figure 12:
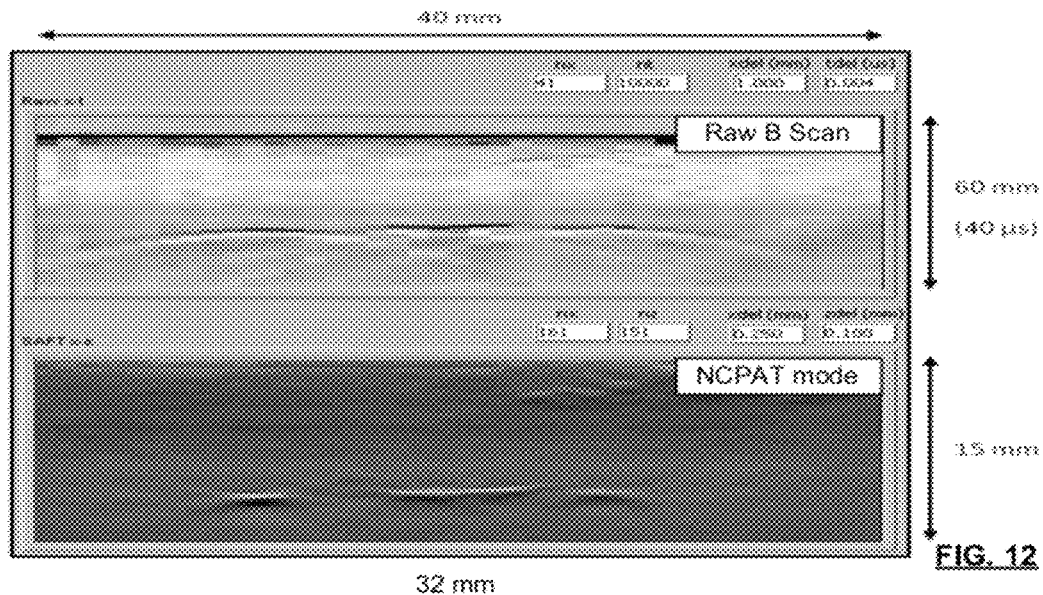
FIG. 12 is a modified print-screen showing a raw B-scan (upper image) and the corresponding SAFT reconstruction (lower image) obtained in NCPAT imaging mode.

The other examples show the capability of the approach to produce good resolution B-scan images by scanning a smaller spot and using reconstruction by SAFT processing. To generate this data, scanning was performed by moving the phantom instead of using a scanning mirror. FIG. 11 shows the preparation of a chicken breast phantom with 3 embedded black polyethylene strips as inclusions. These inclusions were covered by an additional layer of chicken breast tissue (about 12 mm thick). FIG. 12 shows the raw B-scan data (upper image) obtained on this phantom and the SAFT processed data for NCPAT mode (lower image). After reconstruction, the 3 absorbing inclusions are clearly seen. In this case, the detection spot size was 1 mm in diameter and the scanning step was 1 mm. 41 A-scans were used for the reconstruction.

Figure 13:
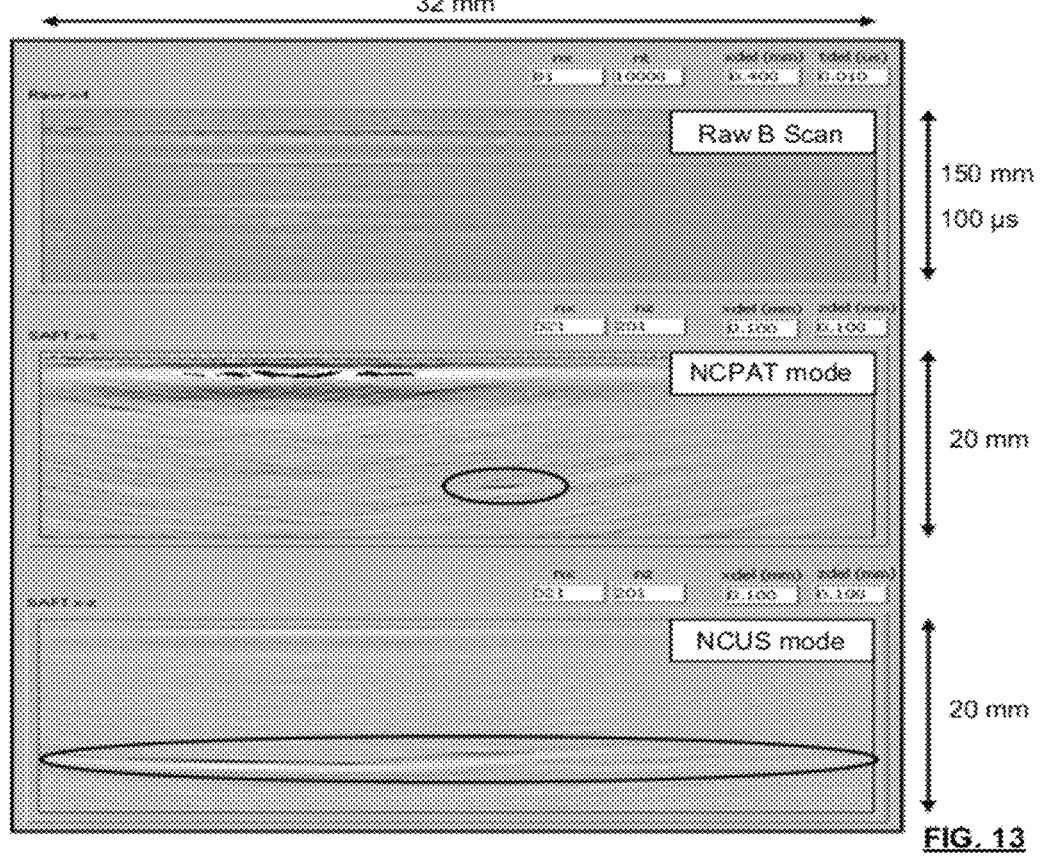
FIG. 13 is a modified print-screen showing a raw B-scan (upper image), the corresponding SAFT reconstruction (middle image) obtained in NCPAT imaging mode, and the SAFT reconstruction (lower image) obtained in NCUS imaging mode.

FIG. 13 shows results obtained on a chicken breast phantom with a single 2 mm wide black polyethylene strip embedded about 15 mm below the surface. They include the raw B-scan data (upper image), the SAFT processed B-scan in NCPAT imaging mode (middle image) and NCUS imaging mode (lower image). When NCPAT is assumed and SAFT is applied accordingly, the inclusion is clearly seen after processing although not distinguishable in the raw data. When a source of ultrasonic wave is assumed to be close to the surface, processing for the NCUS imaging mode shows clearly a small impedance mismatch between the two pieces of chicken breast. In this case the surface has not been dyed but the chicken breast has however some background absorption at the 532 nm wavelength used for generation. Since there is a strong increase of light energy density close to the surface due to scattering, it is then reasonable to assume that there is a source of ultrasound near the surface. In this case interrogation of the phantom is purely acoustic and does not indicate a buried optically absorbing inclusion. These data were obtained with a detection spot diameter and scanning step of 0.4 mm. 81 A-scans were used for the reconstruction.

REFERENCES

The contents of the entirety of each of which are incorporated by this reference:
[1] C. B. Scruby and L. E. Drain, Laser-Ultrasonics: Techniques and Applications, Adam Hilger, 1990.
[2] J.-P. Monchalin, "Optical detection of ultrasound at a distance using a confocal Fabry-Perot interferometer," Appl. Phys. Lett. 47, 14-16 (1985)
[3] J.-P. Monchalin, "Optical detection of ultrasound," IEEE Trans. Ultrason. Ferroelectr. Freq. Control 33, 485-499 (1986)
[4] J.-P. Monchalin, R. K. Ing, Broadband Optical Detection of Transient Motion From a Scattering Surface by Two-Wave Mixing in a Photorefractive Crystal, U.S. Pat. No. 5,131,748.
[5] R. K. Ing and J.-P. Monchalin, Broadband Optical Detection of Ultrasound by Two-Wave Mixing in a Photorefractive Crystal, Appl. Phys. Lett. vol. 59, pp. 3233-3235, 1991.
[6] A. Blouin, P. Delaye, D. Drolet, J.-P. Monchalin and G. Roosen, Sensitive and Fast Response Optical Detection of Transient Motion From a Scattering Surface by Two-Wave Mixing, U.S. Pat. No. 5,680,212.
[7] A. Blouin, J.-P. Monchalin, Detection of ultrasonic motion of a scattering surface by two-wave mixing in a photorefractive GaAs crystal, Appl. Phys. Lett. 65, 932, (1994).
[8] L. V. Wang and H. Wu, Biomedical Optics: Principles and Imaging (John Wiley and Sons, Hoboken, N.J., 2007).
[9] F. A. Duck, "Medical and non-medical protection standards for ultrasound and infrasound," Prog. Biophys. Mol. Biol. 93, 176-191 (2007).
[10] Laser Institute of America, American National Standard for the Safe Use of Lasers ANSI Z136.1-2000 (ANSI, Orlando, Fla., 2000)
[11] T. Berer, A. Hochreiner, B. Reitinger, H. Grün, and P. Burgholzer, "Remote photoacoustic imaging for material inspection", $2^{nd}$ international symposium on laser ultrasonics—Science, Technology and Applications, Jul. 5-8, 2010, Bordeaux, France.
[12] X. Wang, Y. Pang, G. Ku, X. Xie, G. Stoica, and L. V. Wang, "Noninvasive laser-induced photoacoustic tomography for structural and functional in vivo imaging of the brain", Nature Biotech. 21, 803-806 (2003).
[13] S. L. Jacques, P. E. Andersen, S. G. Hanson, and L. R. Lindvold, "Non-contact detection of laser-induced acoustic waves from buried absorbing objects using a dual-beam common-path interferometer", SPIE Proceedings vol. 3224, 307-318 (1998).
[14] B. P. Payne, V. Venugopalan, B. B. Mikic, and N. S. Nishioka, "Optoacoustic tomography using time-resolved interferometric detection of surface displacement", Journal of Biomedical Optics, vol. 8, pp. 273-280 (2003).
[15] H. F. Zhang, C. A. Puliafito, S. J. Jiao, "Photoacoustic Ophthalmoscopy for In Vivo Retinal Imaging: Current Status and Prospects", Ophtahalmic Surgery, Lasers & imaging, vol. 42, pp. S106-S115 (2011).

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. A method for inspecting biological tissue, said tissue having a maximum permissible exposure (MPE) to a laser, the method comprising:
providing biological tissue to be inspected, the biological tissue having an exposed surface;
providing an optical detection system positioned with respect to the biological tissue such that said exposed surface is presented to the optical detection system;
exciting an ultrasonic wave to propagate within the tissue at least near the surface;
emitting a pulsed detection laser beam with said optical detection system onto the surface at a detection spot, the pulsed laser beam having a wavelength at which there is little absorption by the tissue, and a pulse duration chosen with respect to the excitation, to correspond with ultrasonic propagation times associated with a range of distances from the surface, whereby the detection laser is only applied when measuring ultrasonic displacement consistent with sampling the desired range, said emitting being performed below said tissue MPE;
collecting reflected and backscattered light with said optical detection system from the detection spot with large etendue optics; and
demodulating light with said optical detection system collected from the detection spot, to extract information from the ultrasonic wave detected at the detection spot;
wherein said emitting and said collecting are performed without contacting said biological tissue exposed surface with said optical detection system.

2. The method of inspecting according to claim 1 wherein providing the tissue comprises providing in situ tissue.

3. The method of inspecting according to claim 1 wherein exciting the ultrasonic wave is performed without contacting the surface.

4. The method of inspecting according to claim 1 wherein emitting the pulsed detection laser beam comprises selecting the pulse duration with a time delay from the generation pulse to correspond with a subsurface depth range.

5. The method of inspecting according to claim 1 wherein exciting the ultrasonic wave comprises emitting light from a pulsed generation laser extending over a large area of the surface in comparison with a size of the detection spot.

6. The method of inspecting according to claim 1 wherein exciting the ultrasonic wave comprises emitting light from a pulsed generation laser having a wavelength that provides distributed absorption near the surface, providing thermoelastic ultrasonic generation without substantial ablation.

7. The method of inspecting according to claim 1 wherein exciting the ultrasonic wave comprises emitting light from a pulsed generation laser at a wavelength that penetrates into the tissue and generates ultrasonic waves at optical absorbers within the tissue.

8. The method of inspecting according to claim 7 wherein exciting the ultrasonic wave comprises emitting light from a pulsed generation laser at a plurality of different wavelengths to obtain spectroscopic or polychromatic information about the optical absorber.

9. The method of inspecting according to claim 1 wherein exciting and using are repeated and information regarding respective ultrasonic waves is recorded at different locations on the surface, to generate an image of the ultrasound within the tissue.

10. The method of inspecting according to claim 1 further comprising obtaining an image by scanning the detection laser spot over the surface of the tissue and applying a synthetic aperture focusing technique (SAFT) to obtain B-scan or C-scan images.

11. The method of inspecting according to claim 10 wherein SAFT reconstruction is improved by taking into account surface topography which is measured with a profilometer or range finder.

12. The method of inspecting according to claim 10 wherein SAFT reconstruction is improved by taking into account surface topography which is measured by Optical Coherence Tomography.

13. The method of inspecting according to claim 1 further comprising measuring the surface using Optical Coherence Tomography (OCT), and displaying the detected ultrasonic waves and OCT measurement simultaneously.

14. The method of inspecting according to claim 9 wherein generating the image further comprises aligning spot data using an optical scanner.

15. The method of inspecting according to claim 9 wherein generating the image further comprises aligning spot data using a position tracking system.

16. The method of inspecting according to claim 9 wherein generating the image further comprises aligning spot data using a vision-based position tracking system.

17. The method of inspecting according to claim 1 wherein the optical detection system comprises optics mounted within an endoscope.

18. The method of inspecting according to claim 1 wherein exciting the ultrasonic wave comprises emitting light from a pulsed generation laser beam having a detection pulse duration less than 20 µs, a wavelength being 1-2 µm, and an energy density set in accordance with the safety limits (MPE) for biological tissues.

19. The method of inspecting according to claim 1, wherein said emitting a pulsed detection laser beam comprises emitting with a detection laser pulse power maximized to optimize detection sensitivity.

20. The method of inspecting according to claim 1, wherein said biological tissue is a tissue selected from the group consisting of an interface between layers of a retina and a retina-vitreous humor interface.

* * * * *